United States Patent [19]
Yoon

[11] Patent Number: 5,375,588
[45] Date of Patent: Dec. 27, 1994

[54] METHOD AND APPARATUS FOR USE IN ENDOSCOPIC PROCEDURES

[76] Inventor: InBae Yoon, 2101 Highland Ridge Dr., Phoenix, Md. 21131

[21] Appl. No.: 930,929

[22] Filed: Aug. 17, 1992

[51] Int. Cl.$^5$ ............................................... A61B 1/00
[52] U.S. Cl. ............................................ 128/4; 606/1; 604/180; 604/174
[58] Field of Search ............... 604/174, 178, 179, 180; 606/1, 130, 108, 78; 602/6, 41, 58; 128/4, 20, 898, 59, 96.1

[56] References Cited

U.S. PATENT DOCUMENTS

| | | | |
|---|---|---|---|
| 667,768 | 2/1901 | De Puy | 602/6 |
| 1,213,001 | 1/1917 | Philips . | |
| 2,898,917 | 8/1959 | Wallace . | |
| 3,017,887 | 1/1962 | Heyer | 604/178 X |
| 3,039,468 | 6/1962 | Price . | |
| 3,253,594 | 5/1966 | Matthews et al. . | |
| 3,288,137 | 11/1966 | Lund | 604/180 |
| 3,459,175 | 8/1969 | Miller . | |
| 3,817,251 | 6/1974 | Hasson . | |
| 3,856,020 | 12/1974 | Kovac . | |
| 3,952,742 | 4/1976 | Taylor . | |
| 4,077,412 | 3/1978 | Mossun . | |
| 4,083,369 | 4/1978 | Sinnreich . | |
| 4,161,175 | 7/1979 | Bentele | 602/6 |
| 4,213,452 | 7/1980 | Shippert | 602/6 |
| 4,327,716 | 5/1982 | Ansted . | |
| 4,555,242 | 11/1985 | Saudager . | |
| 4,593,681 | 6/1986 | Soni . | |
| 4,608,965 | 9/1986 | Anspach, Jr. et al. . | |
| 4,633,869 | 1/1987 | Schmieding | 606/1 |
| 4,666,433 | 5/1987 | Parks . | |
| 4,670,008 | 6/1987 | Von Albertini . | |
| 4,748,982 | 6/1988 | Horzewski et al. . | |
| 4,944,732 | 7/1990 | Russo . | |
| 4,957,124 | 9/1990 | Mooney | 606/130 X |
| 4,959,055 | 9/1990 | Hillyer | 604/179 |
| 4,985,033 | 1/1991 | Boebel et al. . | |
| 5,002,557 | 3/1991 | Hasson . | |
| 5,009,643 | 4/1991 | Reich et al. . | |
| 5,073,169 | 12/1991 | Raiken . | |
| 5,112,321 | 5/1992 | Hillebrandt . | |
| 5,112,347 | 5/1992 | Taheri . | |
| 5,122,122 | 6/1992 | Allgood . | |
| 5,137,520 | 8/1992 | Maxson et al. . | |
| 5,147,316 | 9/1992 | Castillenti . | |
| 5,176,648 | 1/1993 | Holmes et al. . | |
| 5,176,697 | 1/1993 | Hasson et al. . | |
| 5,183,033 | 2/1993 | Wilk . | |
| 5,201,742 | 4/1993 | Hasson | 606/1 X |

FOREIGN PATENT DOCUMENTS

| | | |
|---|---|---|
| 0432363 | 6/1991 | European Pat. Off. . |
| 1184139 | of 0000 | France . |
| 2653424 | 6/1978 | Germany . |
| 1113896 | 5/1968 | United Kingdom . |

Primary Examiner—Richard J. Apley
Assistant Examiner—Karen A. Jalbert

[57] ABSTRACT

A stabilizer member includes a layer of malleable, shape-retaining material to be disposed on an external surface of tissue forming the wall of an anatomical cavity to allow one or more medical instruments to be inserted through the layer and into the anatomical cavity with the layer stabilizing the instruments longitudinally and angularly relative to the cavity wall. The malleable, shape-retaining properties of the layer allow it to be shaped by a surgeon to a desired configuration to, in turn, provide the cavity wall with a desired configuration creating or increasing the size of a space within the anatomical cavity.

31 Claims, 14 Drawing Sheets

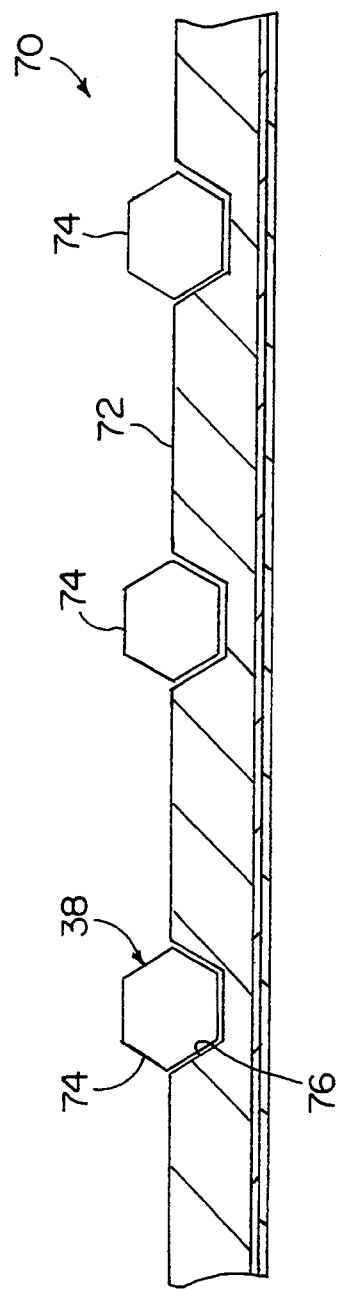

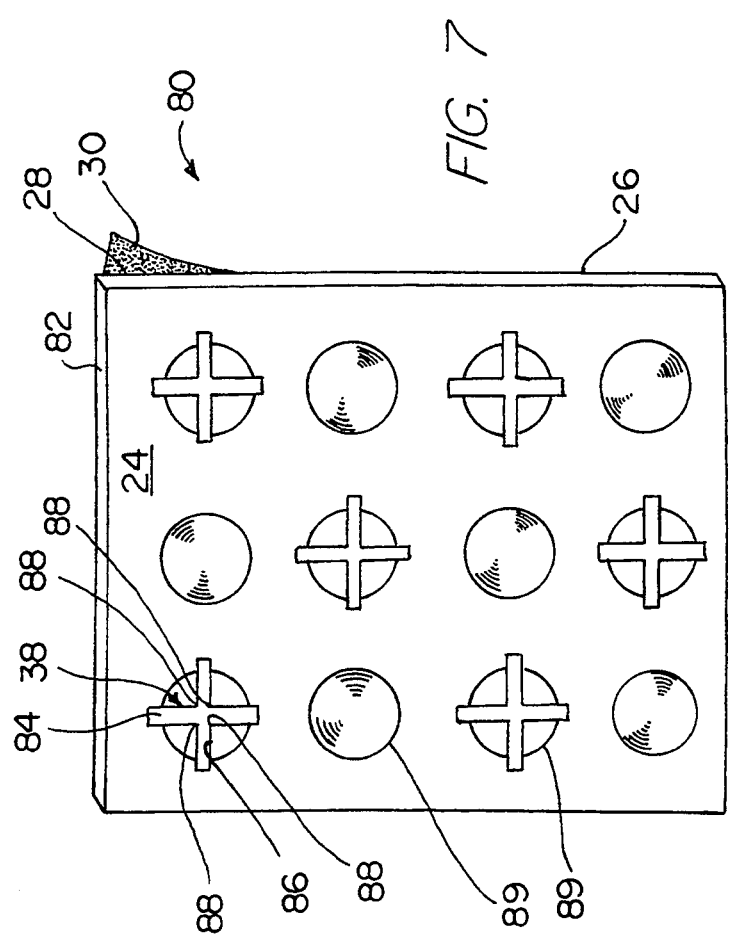

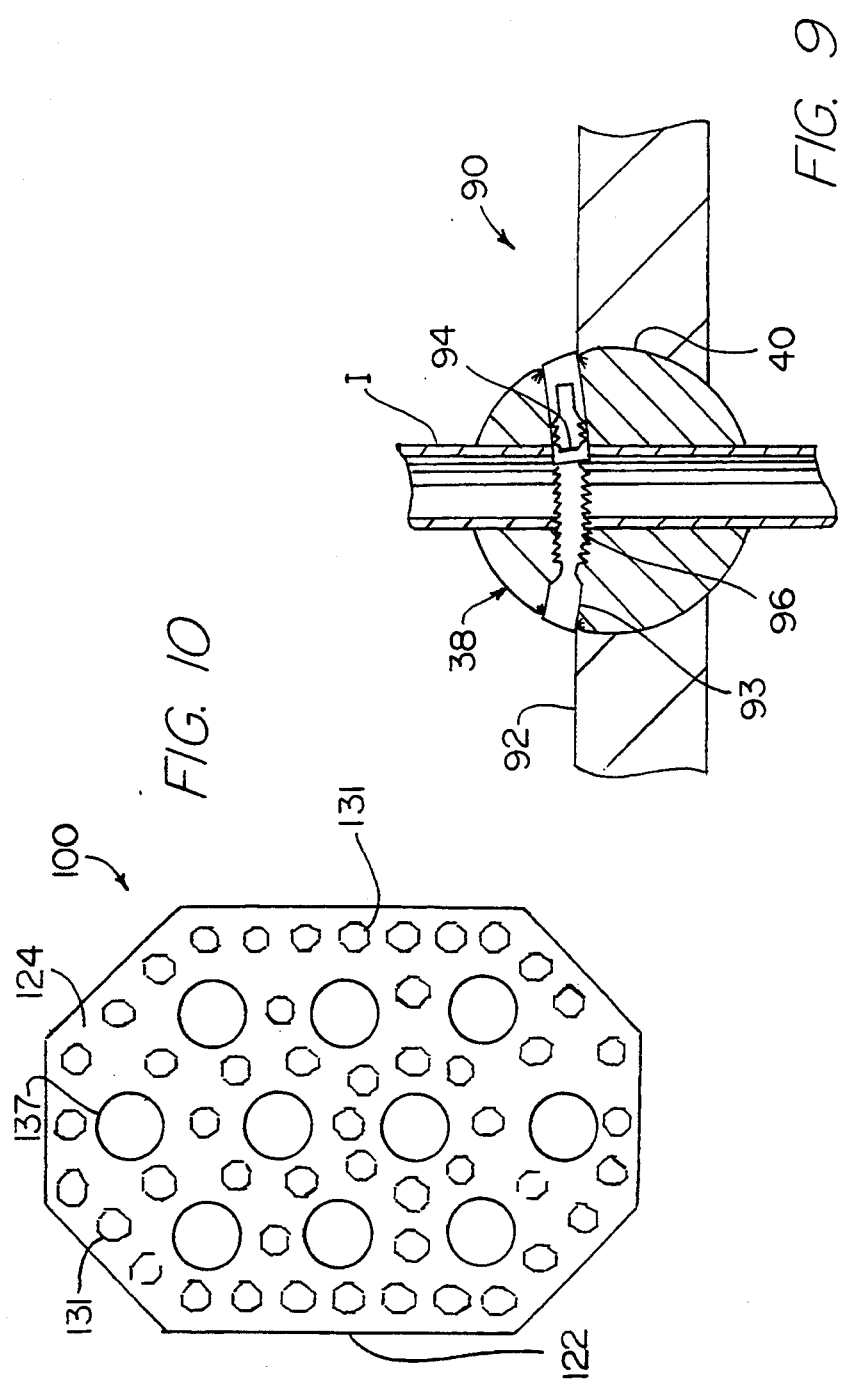

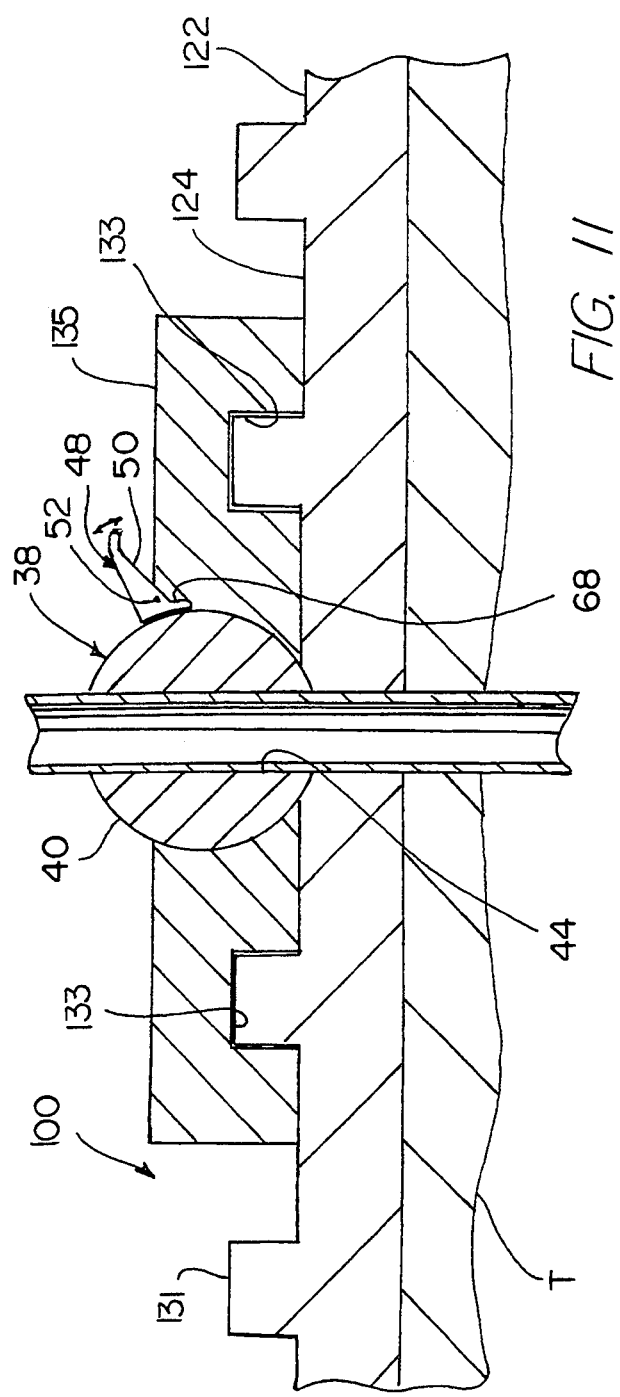

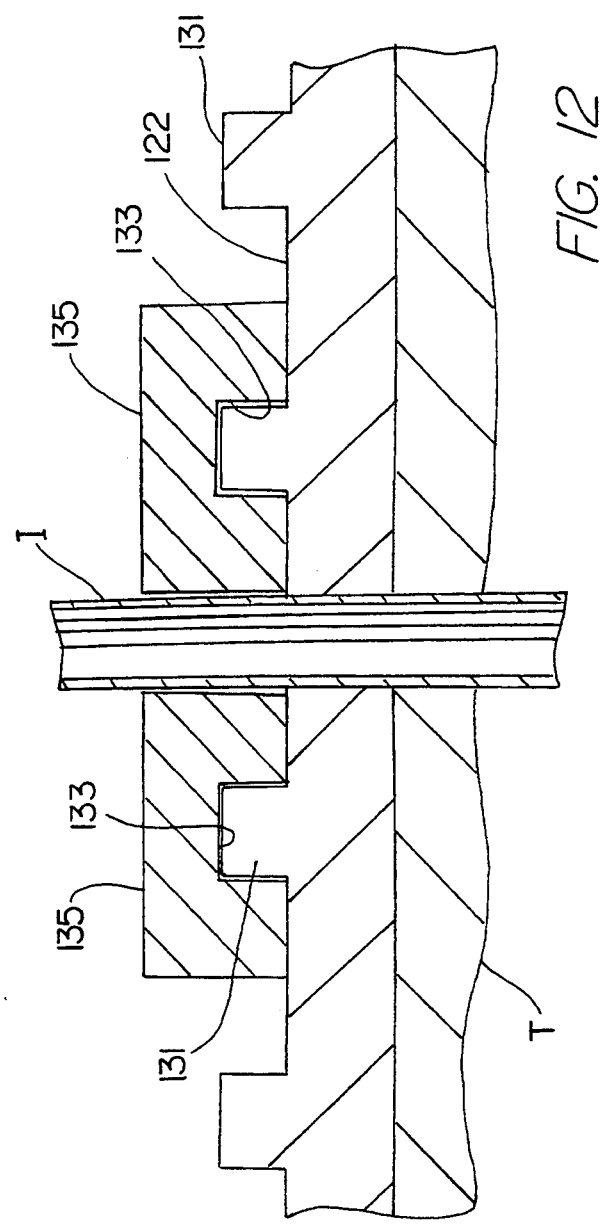

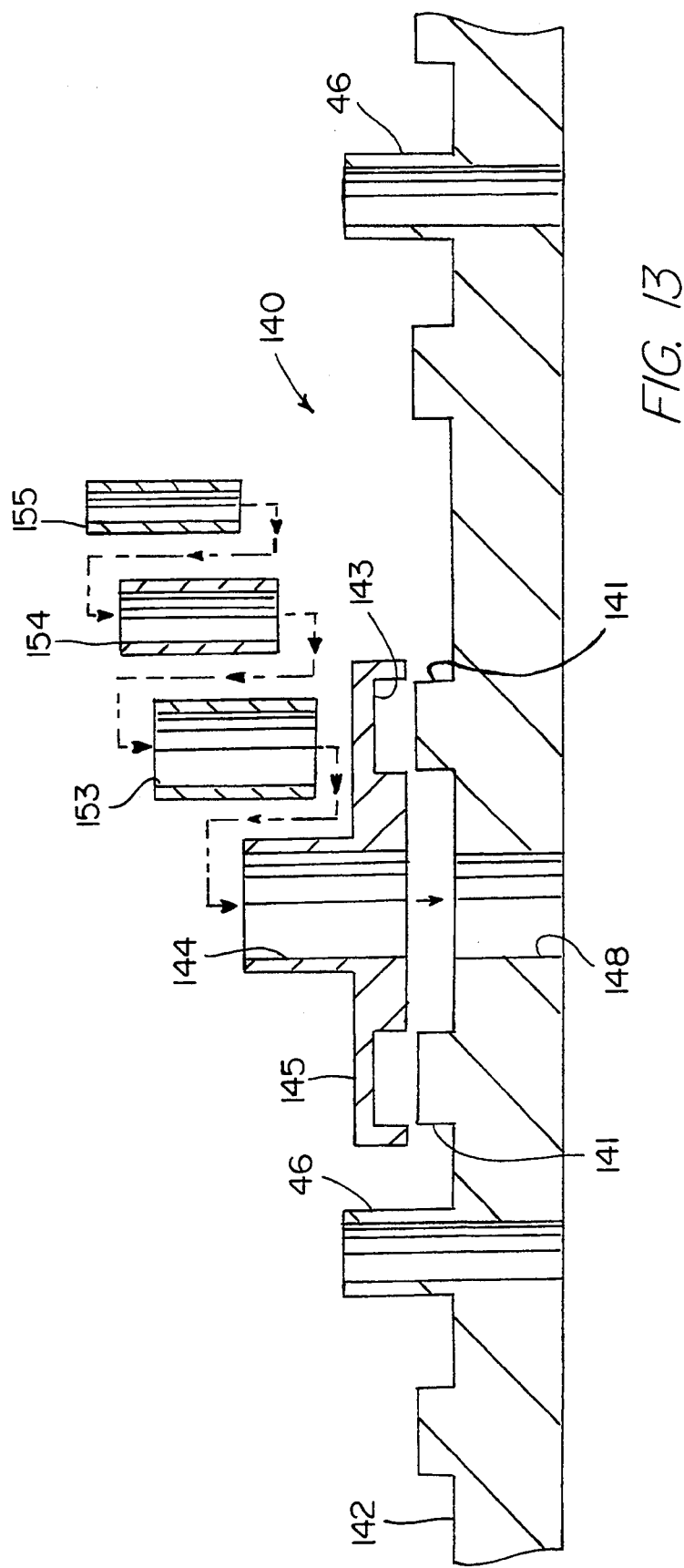

METHOD AND APPARATUS FOR USE IN ENDOSCOPIC PROCEDURES

BACKGROUND OF THE INVENTION

1. Field of the Invention

The present invention pertains to methods and apparatus for endoscopic procedures and, more particularly, to facilitating such procedures by stabilizing surgical instruments inserted in walls of anatomical cavities and shaping the cavity walls to increase safety and visualization.

2. Discussion of the Prior Art

Penetrating instruments having an outer sleeve or cannula and an obturator or penetrating member disposed within the outer sleeve or cannula have become extremely popular for use in surgical procedures to gain access to anatomical cavities, such as the abdomen. Such instruments are used to establish endoscopic portals for many various procedures, most notably laproscopic procedures, with access to the anatomical cavity being established via the outer or portal sleeve positioned to extend through a wall of the cavity upon penetration into the cavity with the penetrating member. Once the portal sleeve extends through the thickness of the cavity wall and projects into the cavity, it is desirable to stabilize or secure the portal sleeve in the cavity wall to prevent withdrawal or backing out of the portal sleeve from the cavity. Additionally, it is desirable in many various procedures to position the portal sleeve at an angle with the cavity wall and to hold the portal sleeve in the angular position to optimize access to tissue and organ structures within the cavity.

Primary and secondary puncture or cavity penetrations are normally accomplished after insufflation of the cavity, such as forming a pneumoperitoneum, to provide increased space for visualization and maneuvering. There are many disadvantages associated therewith, however, such as compressing the diaphragm and respiratory tract and collapsing the lungs.

SUMMARY OF THE INVENTION

Accordingly, it is a primary object of the present invention to overcome the aforementioned disadvantages of prior art methods and apparatus for endoscopic procedures.

Another object of the present invention is to secure a stabilizer member to an external surface of a wall of an anatomical cavity to permit angular and longitudinal stabilizing of medical instruments inserted through the stabilizer member and the cavity wall without engaging tissue within the cavity or cavity wall.

It is also an object of the present invention to attach a malleable, shape-retaining layer to an external surface of tissue forming an anatomical cavity wall for shaping the wall to form or increase the size of a space within the cavity in response to shaping of the layer.

Still another object of the present invention is to provide a locking mechanism for securing a movable joint of a stabilizer member disposed on an external surface of a wall of an anatomical cavity in a selected position to stabilize the position of an instrument inserted through the stabilizer member and into the cavity relative to the cavity wall.

The present invention has a further object in that a stabilizer member can be used to stabilize various types of medical instruments extending through openings in anatomical cavities and to simultaneously stabilize and position more than one medical instrument.

Another object of the present invention is to provide a method of performing endoscopic operative procedures in an anatomical cavity including inserting a portal sleeve through a malleable, shape-retaining layer on an external surface of a wall of the cavity.

An additional object of the present invention is to provide a method of performing endoscopic operative procedures in an anatomical cavity including providing a wall of the cavity with a desired configuration in response to shaping a malleable, shape-retaining layer on an external surface of the cavity wall.

A further object of the present invention is to facilitate visualization and access within anatomical cavities in endoscopic operative procedures without or minimizing the need for insufflation.

Some of the advantages of the present invention are that the stabilizer member does not penetrate or engage tissue within the cavity or the cavity wall, the need for insufflation gas to create a pneumoperitoneum is minimized or eliminated in that the layer can be shaped to form or increase the size of a space within an anatomical cavity, the positions of medical instruments within anatomical cavities can be easily adjusted during endoscopic operative procedures, the layer can be used as a retractor in laparotomy procedures, medical instruments can be stabilized longitudinally and angularly in cavity walls at various positions along the lengths of the instruments and the apparatus can be economically constructed to be disposable for single patient use.

Accordingly, the apparatus of the present invention is characterized in a stabilizer member in the nature of a layer or mat of material to be disposed on an external surface of tissue forming the wall of an anatomical cavity to allow one or more medical instruments to be inserted through the layer and into the anatomical cavity. The medical instruments can be stabilized longitudinally relative to the cavity wall via frictional retention of the instruments with the layer or with orienting portions mounted on or in the layer or via locking mechanisms. The orienting portions are rotatable relative to the layer allowing medical instruments inserted through the orienting portions to be selectively angularly positioned relative to the cavity wall, and the locking mechanisms are selectively movable between locked and unlocked positions to engage and disengage the orienting portions to stabilize the medical instruments in the angular positions. The layer is made from a malleable, shape-retaining material allowing the layer and with it the cavity wall to be shaped to a desired configuration creating a space or increasing the size of a space within the cavity. Methods of stabilizing medical instruments according to the present invention include the steps of placing the layer on the external surface and inserting a medical instrument through the layer and the cavity wall. Methods of performing endoscopic operative procedures according to the present invention include the steps of placing the layer on the external surface and shaping the layer to a desired configuration to, in turn, shape the cavity wall to a desired configuration.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 6 is a broken view, partly in section, of another modification of a stabilizer member according to the present invention.

FIG. 7 is a perspective view of an additional modification of a stabilizer member according to the present invention.

FIG. 9 is a broken view, partly in section, of yet another modification of a stabilizer member according to the present invention.

FIG. 10 is a front view of a further modification of a stabilizer member according to the present invention.

FIG. 11 is a broken sectional view of the stabilizer member of FIG. 10 illustrating the stabilizer member in use with a template.

FIG. 12 is a broken sectional view of the stabilizer member of FIG. 10 illustrating the stabilizer member in use with a pair of templates to stabilize a medical instrument.

FIG. 13 is a broken sectional view of still another modification of a stabilizer member according to the present invention.

DESCRIPTION OF THE PREFERRED EMBODIMENTS

Figure 1:
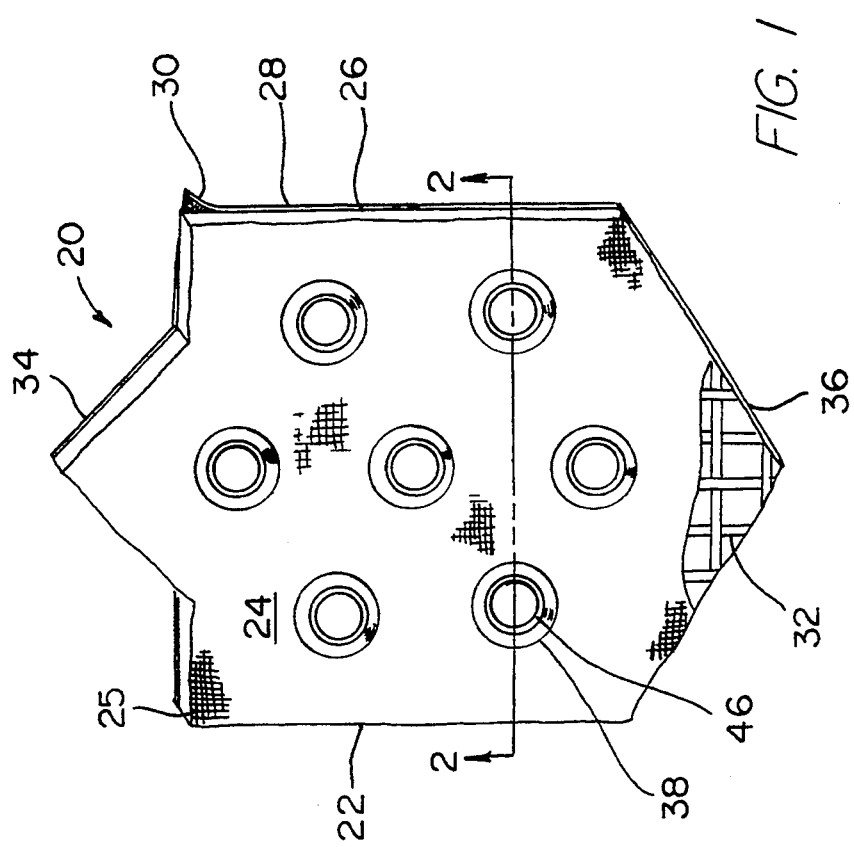
FIG. 1 is a perspective view of a stabilizer member according to the present invention.
Figure 2:
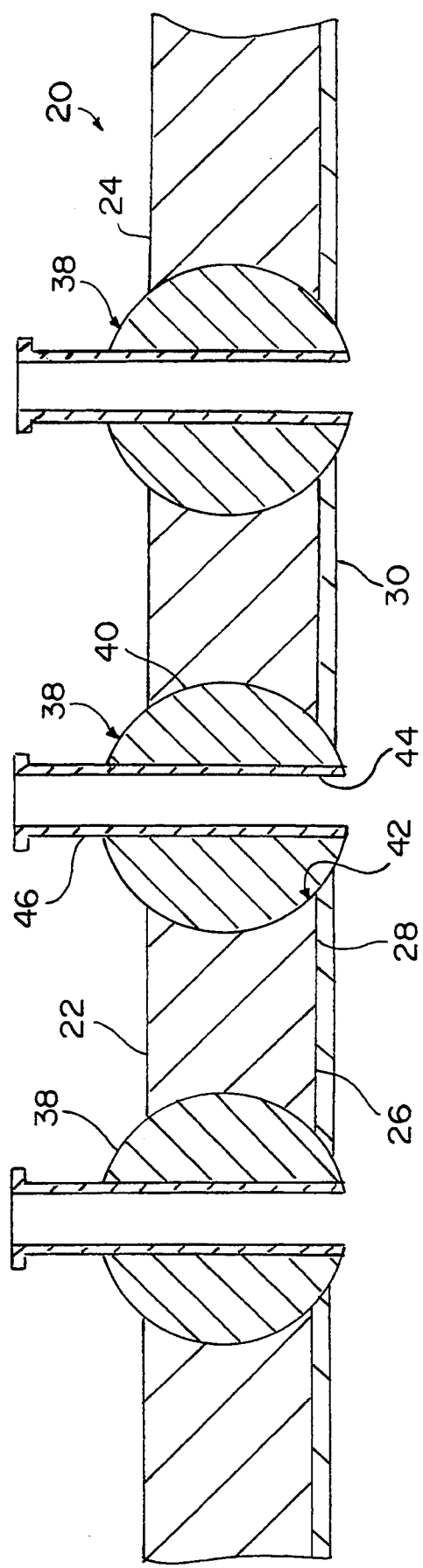
FIG. 2 is a broken sectional view through line 2—2 of FIG. 1.
Figure 3:
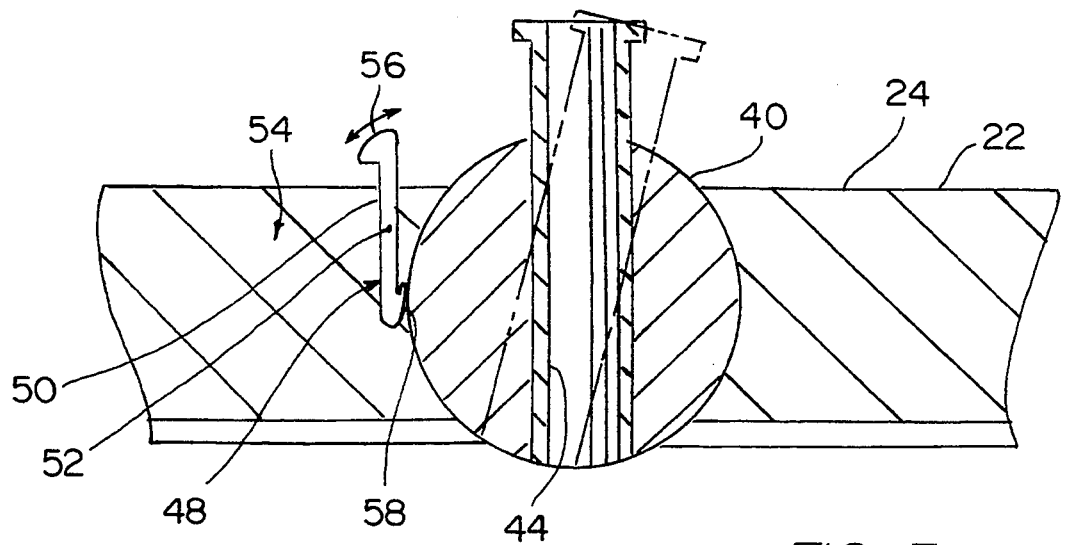
FIG. 3 is a broken sectional view of the stabilizer member of FIG. 1 illustrating positioning of an angularly orienting portion and a locking mechanism for the angularly orienting portion.

An apparatus 20 according to the present invention is illustrated in FIGS. 1–3 and includes a stabilizer member in the nature of a malleable, shape-retaining layer, mat, plate, or panel 22 of transparent, opaque or semi-opaque material having an upper surface 24 that is grooved, formed with recesses or provided with raised irregularities or projections 25, such as bosses, or otherwise roughened to facilitate grasping, a lower surface 26 covered with a coating 28 of adhesive allowing the layer to be attached or secured on an external surface of tissue forming a wall of an anatomical cavity and a removable, protective release sheet 30 disposed over the coating 28. The layer 22 is malleable or bendable to be selectively manually bent, deformed or otherwise shaped to form various tented, domed or bulging configurations and is constructed with sufficient strength and rigidity to retain, once deformed, the deformed configurations. The layer can be made malleable or bendable in many ways, such as by resilient metal strips 32 embedded in the material of the layer, as shown in FIG. 1, or by forming the layer of a suitable semi-rigid, semi-resilient, shape-retaining material, such as plastic, silicone rubber and the like. The layer can be designed to assume predetermined deformed configurations when caused to bend in predetermined directions, or the deformed configuration for the layer can be selected and shaped by the surgeon during use as will be explained further below. By including magnetic particles in the material forming the layer, the layer can be used to hold medical instruments in place. Lead can be included in the material of the layer to provide malleability and strength sufficient to retain various predetermined or selected deformed configurations. The layer can be formed as a solid member, or the layer can be formed as a mesh with openings or interstices allowing flow of air therethrough. The adhesive coating 28 can be formed of any suitable non-tissue reactive adhesive material such as Hollister Medical Adhesive, manufactured by Hollister, Inc., and Elastoplast, manufactured by Biersdorf, Inc. The release sheet 30 can be formed of any suitable paper or plastic material allowing the release sheet to be manually peeled away from the layer to expose the coating 28. The layer can have any surface configuration and size selected in accordance with the desired deformed configuration and the surgical procedure to be conducted. As shown, the layer 22 is generally square in surface configuration with tapered extensions 34 and 36 at opposing ends thereof. The geometric surface configuration of the layer can be selected to encourage movement toward predetermined deformed configurations upon being bent or deformed. In addition to adhesive coating 28, the layer can be attached on the external surface of tissue in many various ways including the use of securing devices such as straps.

A plurality of movable joint members or angularly orienting portions 38 are mounted on or in the layer 22. As shown in FIGS. 2 and 3, joint members 38 include balls 40 rotatably mounted in recesses or sockets 42 in the layer, the balls having axial passageways 44 therethrough and tubular extensions 46 extending outwardly therefrom with lumens of the tubular extensions axially aligned with passageways 44 to provide communication through the layer 22 for a medical instrument. The joint members 38 can be mounted on the upper surface 24 of the layer or within a portion or the entirety of the thickness of the layer, as shown in FIG. 2, and the material of the layer itself can be utilized to frictionally retain the balls within the recesses. The joint members can be arranged on the layer at spaced locations in various asymmetrical or symmetrical patterns to provide great flexibility for the surgeon when introducing medical instruments through the joint members and into anatomical cavities. Balls 40 can be formed of any suitable material such as rubber, plastic and the like, and can be mounted on the layer 22 in many various ways allowing passageways 44 and tubular extensions 46 aligned therewith to be angularly positioned relative to the mat over a range of 360° via rotation of the balls similar to ball and socket joints. The tubular extensions 46 can be formed integrally, unitarily with the balls or the tubular extensions can be formed as separate members mounted in passageways 44 as shown in FIGS. 2 and 3. The extensions 46 can be made of any suitable material, such as rubber, plastic and the like, with lumens sized to grip a medical instrument inserted therethrough to prevent backing out of the instrument and to form a seal therewith. By forming the tubular extensions from resilient, stretchable material, medical instruments of various sizes can be inserted in the passageways 44 with the resilient material of the tubular extensions gripping the medical instruments.

Balls 40, once rotated to position passageways 44 at a desired angle with the mat, can be held with locking mechanisms 48, only a single locking mechanism being shown in FIG. 3. Locking mechanism 48 includes a locking bar 50 pivotally mounted on a pin 52 in a groove or aperture 54 in the layer. The locking bar 50 extends upwardly through the groove 54 to project beyond the upper surface 24 of the layer and terminate at a knob 56 for being grasped by a surgeon. An end of the locking bar disposed within the groove 54 has a hook-like projection or finger 58 thereon for being selectively engaged and disengaged with the ball 40 in response to rotation of the locking bar around pin 52. The locking bar is pivotal between unlocked and locked positions in a plane containing the axis of passageway 44, as shown by the arrow in FIG. 3, such that movement of knob 56 in the direction of tubular extension 46 disengages the finger 58 from the ball 40 in the unlocked position for the locking mechanism while movement of the knob in a direction away from the tubular extension causes finger 58 to engage and secure ball 40 in the locked position for the locking mechanism. Locking bar 50 can be biased, such as by a torsional bias, to the locked position to automatically engage ball 40 upon release of knob 56 from the unlocked position.

Figure 4A:
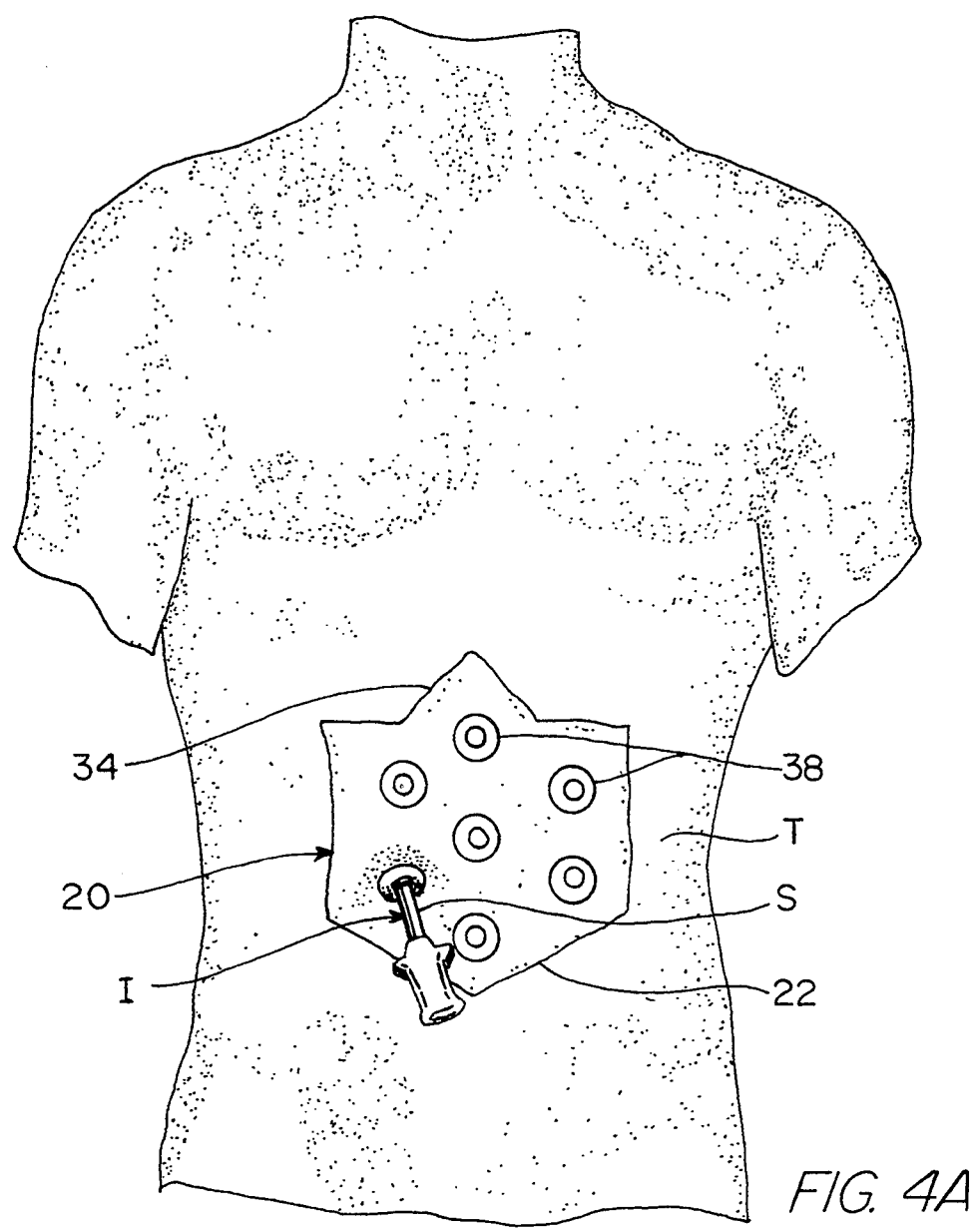
FIG. 4A is a broken view of the stabilizer member of FIG. 1 illustrating the stabilizer member disposed on the external surface of the wall of the abdominal cavity.
Figure 4B:
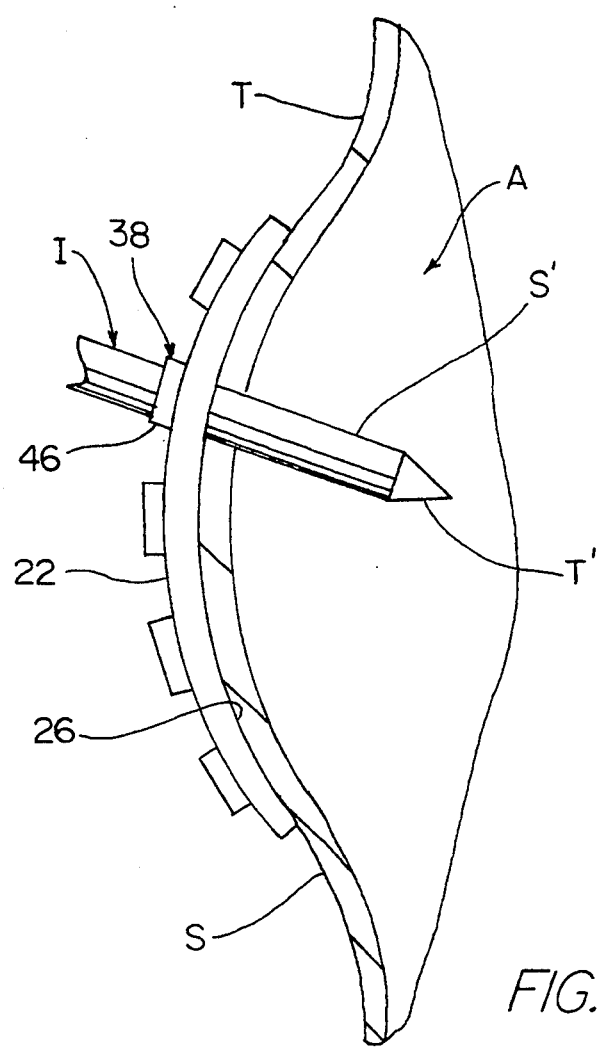
FIG. 4B is a broken view, partly in section, of the stabilizer member of FIG. 1 in a deformed configuration shaping the wall of the abdominal cavity.

To use the apparatus 20 in endoscopic operative procedures, release sheet 30 is manually grasped and peeled away from the layer 22 to expose the adhesive coating 28 on lower surface 26. The layer 22 is positioned over a layer of tissue T forming the wall of an anatomical cavity, such as the abdomen A, as shown in FIGS. 4A and 4B. The lower surface 26 is placed on the external surface, such as skin S, of the tissue and is secured thereto with adhesive 28. Where layer 22 is disposed over the abdomen as shown, tapered extension 34 is aligned with the xiphoid process to permit use of the layer as a template for a particular procedure to be performed with joint members 38 positioned at desired locations for introduction of portal sleeves or other instruments. The surgeon then shapes or deforms, such as by bending, the layer 22 with one or both hands placed upon upper surface 24 to obtain a tented, domed or bulging configuration. The layer 22 will remain in the deformed configuration; and, accordingly, the tissue T is lifted outwardly from the patient's body by the layer to provide the cavity wall with a desired configuration, the tissue T including skin, fat, muscle and peritoneum in the case of laproscopic procedures. With the tissue T forming the cavity wall lifted outwardly, or upwardly, from the patient's body, a space is formed within the cavity between the tissue and organ structure or tissue within the cavity or the size of an existing space is increased such that room for visualization and access is created without the need for insufflation. A penetrating instrument I, typically including a portal sleeve S' and a penetrating member or obturator such as a trocar T' disposed within the portal sleeve, is inserted through the lumen of a tubular extension 46 and passageway 44 of one of the joint members 38 to extend through layer 22 and into the tissue T. The penetrating instrument is utilized to penetrate the tissue T and enter the anatomical cavity, and the penetrating member is typically removed from the penetrating instrument leaving the sleeve S' in place within the cavity. The joint member 38 utilized to enter the anatomical cavity with the penetrating instrument will depend upon the surgical procedure being performed; and, by providing a plurality of joint members 38 at various spaced locations along the plate 22, great flexibility is provided to the surgeon in inserting one or more medical instruments. The sleeve S' will be frictionally gripped or clamped by the tubular extension 46 thusly creating a seal therewith and preventing backing out or inadvertent withdrawal of the sleeve from the anatomical cavity. The longitudinal distance that the sleeve S' extends into the anatomical cavity can be adjusted by manually moving the sleeve longitudinally through the joint member 38 overcoming the gripping force of the tubular extension. The locking bar 50 can be moved to the unlocked position, allowing the sleeve to be rotated and positioned at a desired angle with the cavity wall. The range of angular adjustability for the sleeve can be increased by forming the layer of minimal thickness. Once the sleeve is in a desired angular position relative to the wall of the anatomical cavity, the locking bar 50 can be moved to the locked position to engage ball 40 with projection 58 and hold the sleeve in the angular position. Various medical instruments can be inserted through the sleeve to perform various diverse procedures within the anatomical cavity, and the longitudinal and angular positions of sleeve S' can be readjusted in accordance with the desired position for the instruments. Where the layer includes magnetic particles, medical instruments to be used during the operative procedure can be placed and held thereon. Should it become necessary to access the anatomical cavity via a longitudinal incision, such as in laparotomy, the incision can be made through the layer 22 and the layer used as a retractor.

Figure 5:
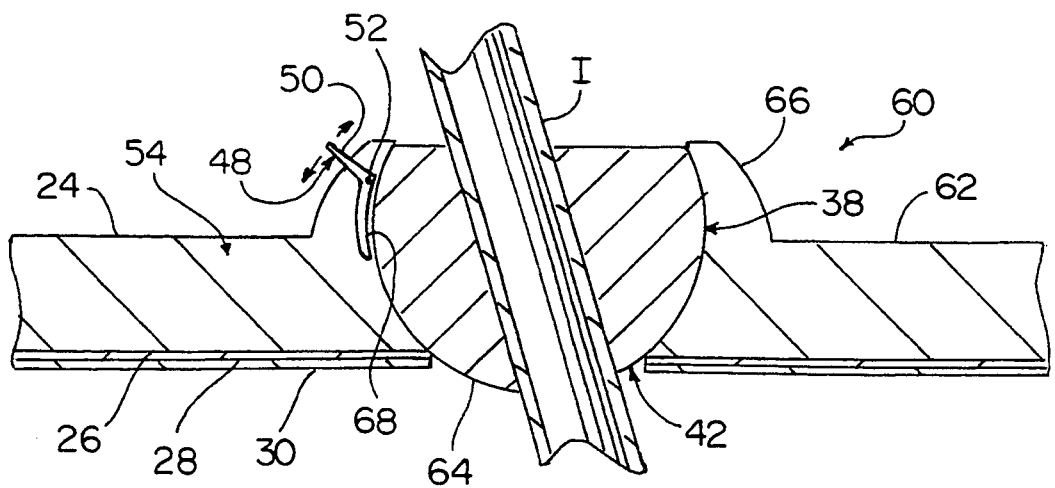
FIG. 5 is a broken sectional view of a modification of a stabilizer member according to the present invention.

A modification for the apparatus according to the present invention is shown at 60 in FIG. 5 wherein only a single angularly orienting portion or joint member 38 is shown. Apparatus 60 includes layer 62 having an upper surface 24, a lower surface 26 with an adhesive coating 28 thereon and a removable release sheet 30 disposed over the coating 28 as previously described. A plurality of joint members 38 are disposed at various spaced locations along the layer 62 to allow communication therethrough by a medical instrument I. Each joint member 38 includes a ball member 64 having a truncated spherical configuration mounted in a mating recess 42 in the layer. An annular flange 66 formed as part of the upper surface 24 extends around the ball 64 and has an inward curvature in cross-section to extend over the ball and prevent removal of the ball from recess 42. Ball 64 can be formed with an axial passageway, or the ball can be made from a penetrable or puncturable material allowing the medical instrument I to be inserted through the joint member 38 without the need for a preformed passageway. A locking mechanism 48 for holding the ball 64 in a desired rotational position includes a locking bar 50 mounted in a groove 54 in the mat and having an end terminating externally of upper surface 24, the locking bar being pivotally mounted within the groove by a pin 52. Locking bar 50 is angularly joined to a locking plate 68 movable between a locked position wherein the locking plate 68 frictionally holds the ball in position and an unlocked position wherein the locking plate is disengaged from the ball in response to rotation of the locking bar.

Layer 62 is utilized in the same manner as previously described for apparatus 20, except that the medical instrument I is utilized to puncture the ball 64 of the joint member 38 through which the instrument is being inserted. Accordingly, the instrument will extend through the ball 64 and be frictionally gripped and held thereby to prevent withdrawal or backing out of the instrument from the anatomical cavity. Where the balls 64 do not extend entirely through the thickness of the layer but, rather, are mounted on the upper surface 24 or within a portion of the thickness of the layer, the layer or portions thereof can be formed of a penetrable material allowing the medical instrument to be inserted therethrough and into the anatomical cavity following penetration through the balls 64.

Another modification of an apparatus according to the present invention is shown in FIG. 6 at 70 and includes a layer 72 substantially the same as the layers 22 and 62 previously described; however, the joint members 38 for the apparatus 70 have a non-circular, non-spherical configuration, being formed as polygon configured members 74 having a hexagonal configuration in cross-section. Members 74 are rotatably or pivotally mounted within recesses 76 in layer 72 allowing a medical instrument inserted through the members to be angularly adjusted relative to the wall of an anatomical cavity. The members 74 and recesses 76 can have various configurations permitting rotation or pivotal movement of the members 74 relative to the layer 72 and, therefore, the wall of an anatomical cavity.

A further modification of an apparatus according to the present invention is shown at 80 in FIG. 7 and includes a layer 82 having an upper surface 24, a lower surface 26 with an adhesive coating 28 and a release sheet 30 disposed over the coating 28 as previously described. Joint members 38 for layer 82 include pairs of intersecting slits 84 and 86 forming a passage through the thickness of the layer 82 to define four tabs or fingers 88. A plurality of circular recesses 89 can be provided in the upper surface 24 to facilitate grasping of the layer 82 by the surgeon, and the slits 84 and 86 can be disposed in the recesses 89 as shown in FIG. 7.

Figure 8:
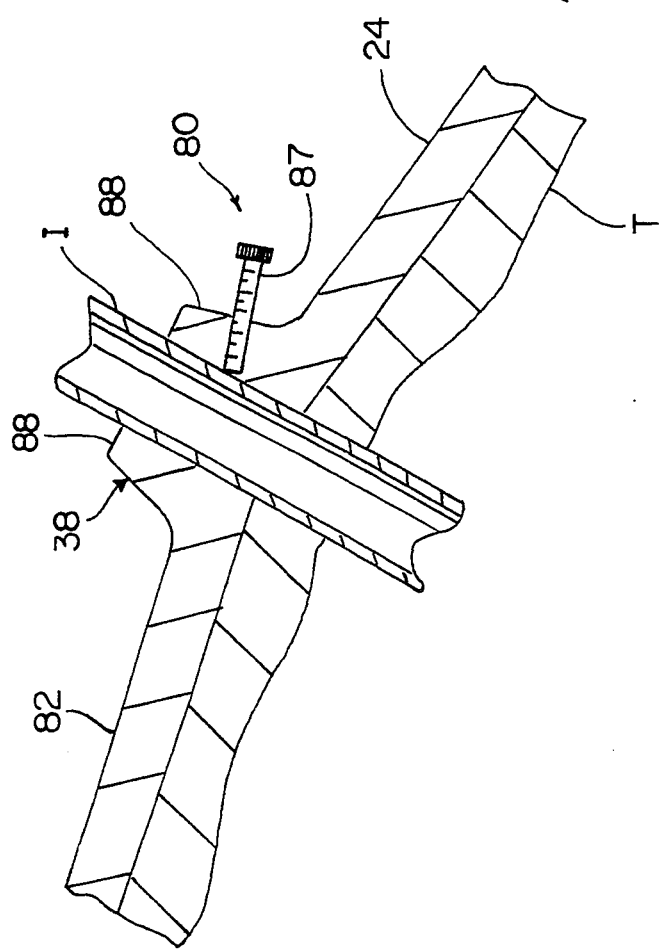
FIG. 8 is a broken view, partly in section, of the stabilizer member of FIG. 7 illustrating the stabilizer member disposed on the external surface of tissue forming the wall of an anatomical cavity.

The apparatus 80 is utilized in a manner similar to that previously described. After the layer 82 is secured on an external surface of tissue T forming a wall of an anatomical cavity, a medical instrument I is inserted through the slits 84 and 86 of a selected joint member 38, as shown in FIG. 8. The tabs 88 can be manually lifted in a direction outwardly from the upper surface 24 or the surgical instrument can be backed out from the layer 82 a short distance such that the tabs or fingers 88 extend around the medical instrument in a direction outwardly from the upper surface to grip and form a seal with the surgical instrument and prevent longitudinal movement of the instrument relative to the cavity wall. By forming the tabs 88 of a resilient material, angular positioning of the medical instrument relative to the wall of the anatomical cavity can be accomplished. By forming the tabs 88 of a shape-retaining material, the fingers themselves can be utilized to secure the medical instrument in a selected angular position without the need for a locking mechanism. Where a locking mechanism is desired, a set screw 87 can be rotatably inserted through one of the tabs 88 to frictionally engage the medical instrument I and thusly prevent longitudinal and angular movement thereof.

FIG. 9 illustrates at 90 another modification of the apparatus according to the present invention including a layer 92 and at least one joint member 38 including a ball 40 as previously described. A clamp 93 formed as a band of material is wrapped around ball 40 of joint member 38 with one end of the band being inserted in a slot 94 in the other end of the band. The end of the band inserted into the slot 94 can have protrusions, notches or serrations thereon, such as teeth 96, for holding the band 92 in tightened condition around the ball 40. Accordingly, the band 92 compresses the ball firmly against medical instrument I inserted therethrough to prevent longitudinal movement of the medical instrument relative to an anatomical cavity wall. Although the clamp 93 is shown in connection with ball 40, it will be appreciated that the clamp can be utilized with various non-circular, non-spherical joint members or angularly orienting portions.

Another embodiment of an apparatus according to the present invention is illustrated at 100 in FIGS. 10 and 11. Apparatus 100 includes a layer 122 having an upper surface 124 and a lower surface to be placed on an external surface of tissue forming the wall of an anatomical cavity. A plurality of engaging members or posts 131 are disposed on the upper surface 124 at spaced locations thereon for being cooperatively engaged in apertures 133 of one or more adapters blocks, only a single block 135 being shown in FIG. 11. Block 135 has recesses or apertures 133 therein, arranged in accordance with the spacing for the posts 131 on layer 122 allowing the block to be secured, via interlocking engagement with posts 131, at various selective locations upon the upper surface 124. A joint member 38 including a ball 40 is rotatably mounted in the block with a passageway 44 extending axially through the ball. A locking mechanism 48 including a pivotal locking bar 50 can be rotatably mounted on the block in a groove via a pin 52 for selectively engaging and disengaging a locking plate 68 with the ball 40 in locked and unlocked positions of the locking mechanism.

In operation, the layer 122 is placed on an external surface of tissue T forming a wall of an anatomical cavity, and a block 135 is positioned on the upper surface 124 to align joint member 38 with a location through which insertion of a medical instrument I is desired. The layer can be formed with a plurality of holes to be aligned with the joint members 38, or circular rims 137 can be provided on the upper surface to facilitate alignment of the joint members 38 with portions of the layer as shown in FIG. 10. Where the layer is not provided with holes, the layer can be formed of a penetrable material allowing insertion of a medical instrument therethrough via the joint members of the template. Once inserted through the tissue T, instrument I can be angularly positioned relative to the wall of the anatomical cavity via rotation of the ball 40.

In a modification, a medical instrument can be inserted directly through the layer 122 without passing through a block, and then a plurality of blocks 135 can be mounted on the upper surface of the layer in engagement with the medical instrument, as shown in FIG. 12, wherein two blocks 135 are disposed on opposite sides of the instrument such that the blocks serve to frictionally engage and stabilize the instrument in position longitudinally and angularly.

A still further modification of an apparatus according to the present invention is shown in FIG. 13 at 140. Apparatus 140 includes a layer 142 that is similar to layer 122 except that the layer 142 includes a plurality of tubular extensions 46 formed integrally, unitarily with the layer for allowing passage of medical instruments therethrough. Layer 142 includes a plurality of holes 148, only one of which is shown, for allowing a medical instrument to be inserted therethrough, and the holes 148 can be aligned with passageways 144 formed in adapter blocks 145 having apertures or recesses 143 for interlocking engagement with posts 141 disposed on an upper surface of the layer 142, only a single block being shown in FIG. 13. With the passageway 144 of the block 145 aligned with one of the holes 148, a medical instrument can be inserted through the layer via the block. Where a medical instrument smaller in size than the diameter of the passageway 144 is to be inserted, adapter sleeves 153, 154 or 155 corresponding in size to the size of the medical instrument to be inserted can be placed in the passageway of the block for gripping the instrument to provide a seal therewith as well as to prevent longitudinal movement of the instrument relative to an anatomical cavity wall.

Figure 14:
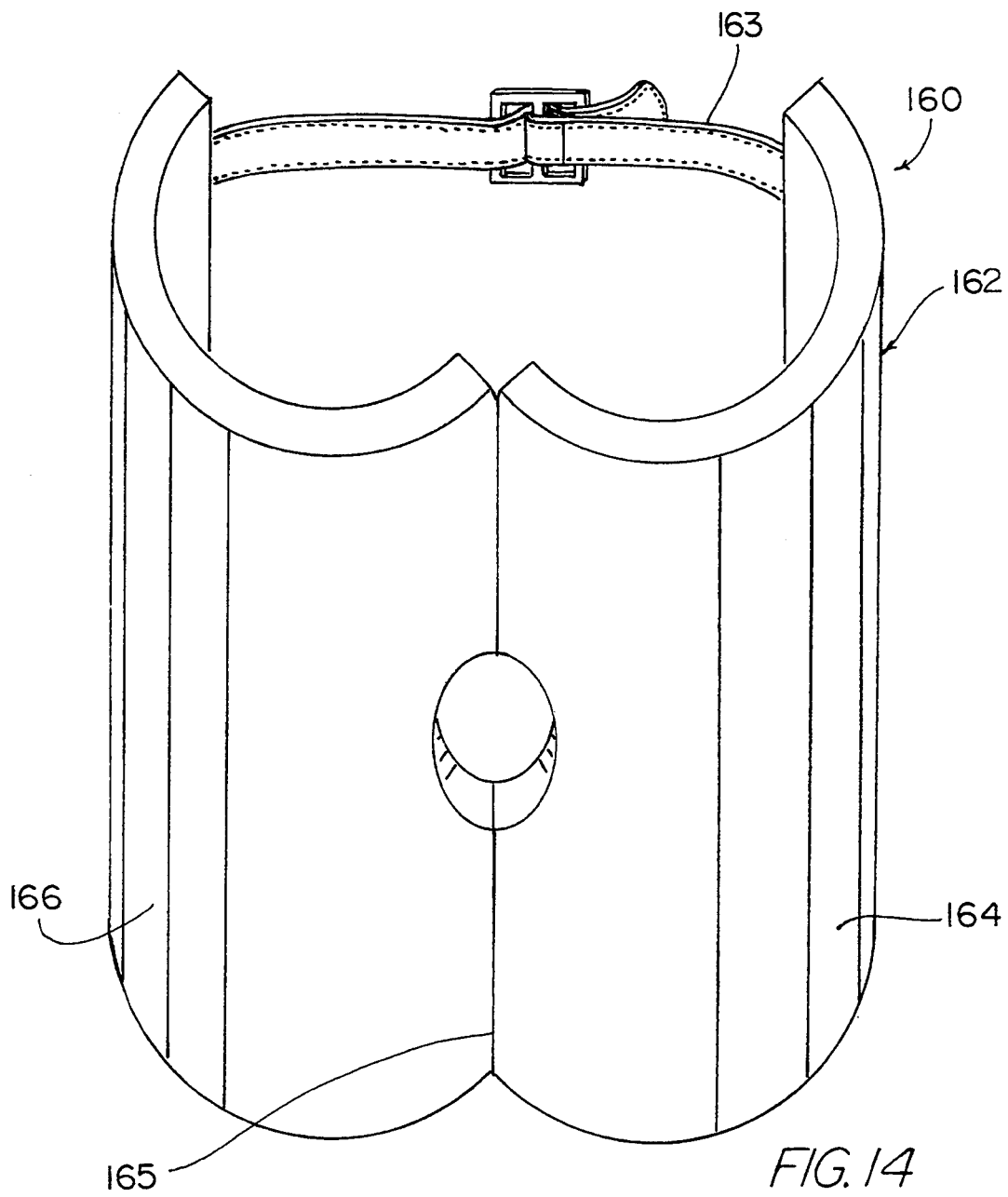
FIG. 14 is a perspective view of another modification of a stabilizer member according to the present invention.

An additional modification of an apparatus according to the present invention is shown at 160 in FIG. 14 and includes a member 162 formed of shaped portions 164 and 166 having a configuration to be placed over an anatomical body part, such as the abdomen or leg, the portions 164 and 166 having opposing lateral ends connectible by means of an adjustable strap 163 allowing the member 162 to be secured on an external surface of a wall of the anatomical body part without the need for adhesive. The inner edges of the portions meet at a joint or hinge 165 of a frictional construction such that when the portions 164 and 166 are pivoted to a desired orientation, the joint will maintain a desired shape for member 162. Member 162 can be formed of a plurality of portions and joints, and a plurality of joint members can be positioned at various spaced locations for introducing medical instruments through the member and into the anatomical body part while stabilizing the instruments longitudinally and angularly relative to the external surface of the body part.

Figure 15:
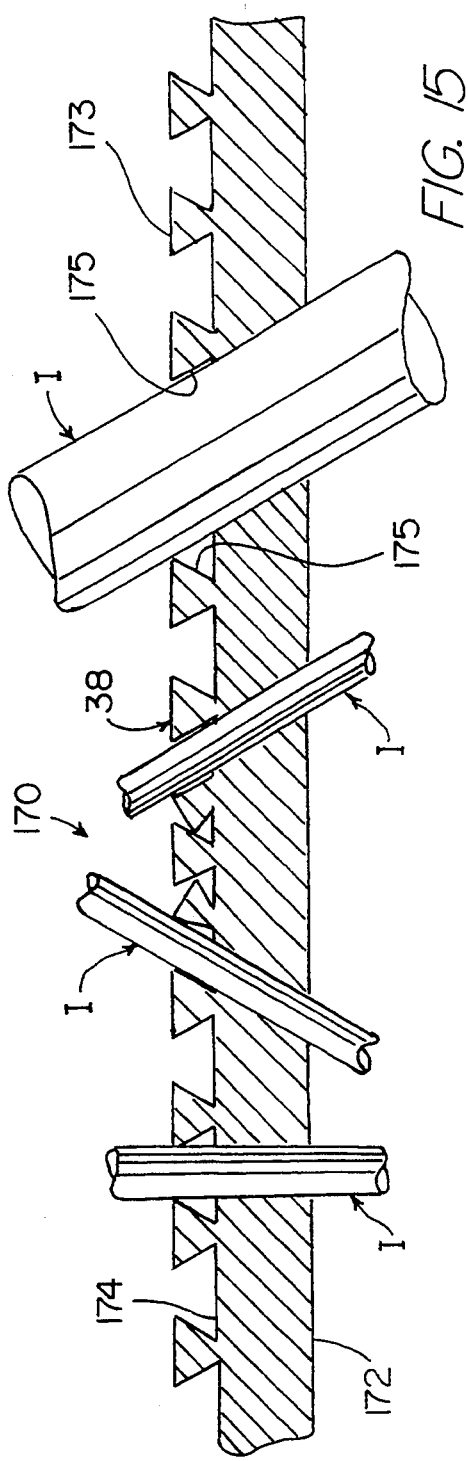
FIG. 15 is a broken view, partly in section, of an additional modification of a stabilizer member according to the present invention.

Another modification of an apparatus according to the present invention is illustrated in FIG. 15 at 170 and includes a layer 172 of malleable, shape-retaining material to be placed on an external surface of tissue forming a wall of an anatomical cavity as previously described. A plurality of joint members or angularly orienting portions 38 are disposed on an upper surface 174 of layer 172 at spaced locations and include nubs 173 that taper outwardly from the surface 174 to provide a conical or pyramidal configuration, shown as triangular in cross-section in FIG. 15, to frictionally engage medical instruments I inserted through the layer 172 in the spaces defined between the nubs. Accordingly, angled surfaces 175 or the upper edges of the nubs frictionally engage the medical instruments preventing backing out of the instruments from the cavity wall while allowing the instruments to be selectively angularly positioned relative to the cavity wall. Where the space between the nubs is too small to accommodate a medical instrument to be inserted, one or more nubs can be cut or broken away from the surface 174 to form a space between remaining nubs large enough in size to receive the instrument.

Figure 16:
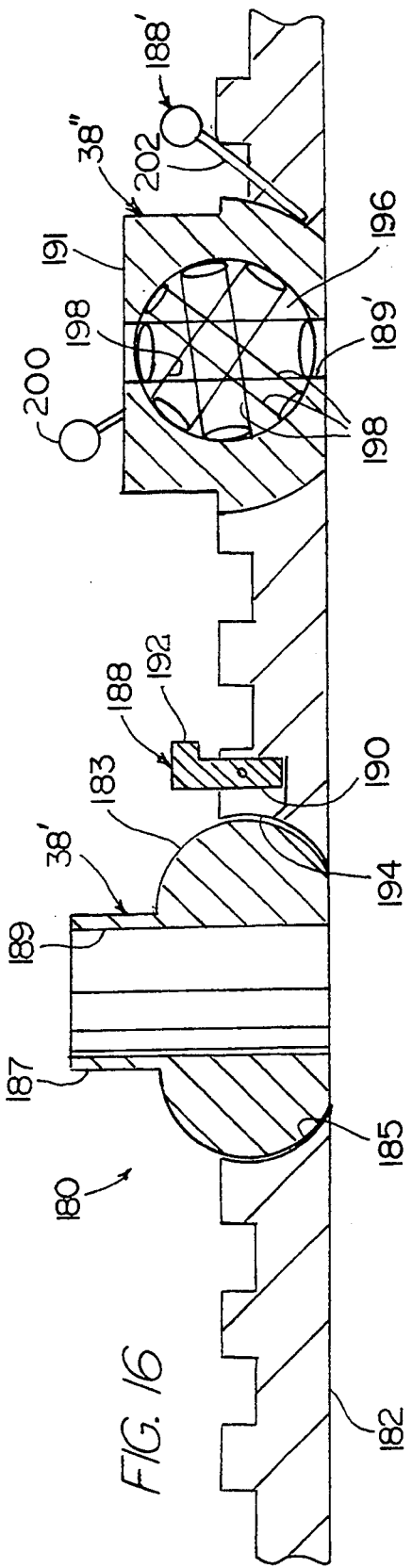
FIG. 16 is a broken sectional view of a further modification of a stabilizer member according to the present invention.

An additional modification of an apparatus according to the present invention is shown in FIG. 16 at 180 and includes a malleable, shape-retaining layer 182 having joint members or angularly orienting portions 38' and 38" mounted thereon. Joint member 38' includes a toroid or donut-shaped base 183 mounted in a curved recess 185 in the layer 182 such that the joint member 38' can rotate to selectively angularly position a medical instrument passing therethrough relative to an anatomical cavity wall. A tubular extension 187 formed integrally, unitarily with the base 183 extends outwardly therefrom and defines a passageway 189 through the joint member for receiving a medical instrument. A locking mechanism 188 is pivotally mounted on the layer 182 and includes a locking bar 190 terminating at a handle 192 externally of the layer and a locking plate 194 movable into and out of engagement with base 183 to secure the base in selective rotational positions. Joint member 38" includes a body 191 rotatably or pivotally mounted on layer 182. The body 191 can have any suitable spherical, curved, or non-curved multi-sided configuration allowing the body to rotate or pivot relative to layer 182. Body 191 rotatably houses a multiluminal, cylindrical or spherical member 196 having a plurality of different size lumens 198 formed therein to be selectively alignable with a passageway 189' formed in the body 191 to provide communication through the joint member 38". An operating member 200 mounted on member 196 extends through body 191 to be manually grasped by a surgeon to align a selected one of the lumens 198 with the passageway 189' in accordance with the size of a medical instrument to be inserted through the layer. A locking mechanism 188' for securing the rotational position of the body 191 includes a pin 202 longitudinally movable into and out of engagement with body 191 via a knob disposed externally of the joint member 38".

The features of the apparatus and method of the present invention described above can be combined as desired for particular procedures to be performed and to suit the desires and needs of individual surgeons. For example, the stabilizer member need not be of shape retaining construction if it is desired to use the apparatus only for stabilizing instrument or if the member is to be grasped by the hand or by external devices to shape the cavity wall; and, of course, even when the stabilizer member is of shape retaining construction, it can be grasped by the hand or by external devices after shaping to assist in maintaining the desired shape. When the apparatus is used to form a tented or domed cavity, it is particularly advantageous for safe introduction of penetrating instruments, such as trocars, thereby eliminating or minimizing the need for prior insufflation.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of performing endoscopic operative procedures in an anatomical cavity comprising the steps of
   attaching a stabilizer member including a malleable, shape-retaining layer to an external surface of a wall of the anatomical cavity;
   shaping the malleable, shape-retaining layer to a desired configuration to, in turn, provide the cavity wall with a desired configuration;

inserting an instrument through the stabilizer member and the cavity wall to enter the anatomical cavity;

adjusting the longitudinal and angular position of the instrument relative to the cavity wall; and gripping the instrument with the stabilizer member to maintain the instrument in the adjusted longitudinal and angular position.

2. The method as recited in claim 1 wherein the instrument is a penetrating instrument including an obturator within a portal sleeve, and said adjusting step includes withdrawing the obturator from the portal sleeve and adjusting the longitudinal and angular position of the portal sleeve relative to the cavity wall.

3. The method as recited in claim 2 wherein said inserting step includes inserting a plurality of portal sleeves at spaced positions through the stabilizer member and the cavity wall to provide access to the anatomical cavity at a plurality of spaced locations.

4. The method as recited in claim 1 wherein said shaping step includes shaping the malleable, shape-retaining layer to move the cavity wall in a direction outwardly from the anatomical cavity to have a domed configuration increasing the space between tissue and organ structures in the anatomical cavity and the cavity wall.

5. The method as recited in claim 4 and further comprising the step of grasping the malleable, shape-retaining layer to maintain the domed configuration.

6. A method of performing endoscopic procedures in an anatomical cavity of the body comprising the steps of attaching a shape-retaining member to an outer surface of a wall of the cavity;

deforming the member to have a desired shape to provide the cavity wall with a corresponding shape thereby altering the shape of the cavity; and performing an endoscopic procedure in the cavity.

7. A method of performing endoscopic procedures as recited in claim 6 wherein said performing step includes penetrating the shape-retaining member and the cavity wall with a penetrating instrument having an obturator within a portal sleeve to provide access to the cavity.

8. A method of performing endoscopic procedures as recited in claim 7 wherein said performing step includes withdrawing the obturator from the portal sleeve and passing another instrument through the portal sleeve.

9. A method of performing endoscopic procedures as recited in claim 6 wherein said performing step includes penetrating the cavity wall and spaced portions of the shape-retaining member with a plurality of penetrating instruments each having an obturator within a portal sleeve to provide a plurality of spaced access portals to the cavity.

10. A method of performing endoscopic procedures as recited in claim 9 wherein the spaced portions of the shape-retaining member are arranged to designate areas of penetration for the penetrating instruments relating to a specific procedure to be performed.

11. Apparatus for facilitating the performance of endoscopic procedures in an anatomical cavity in the body comprising a layer of deformable, shape-retaining material for attachment to an outer surface of a wall of the cavity;

means carried by said layer of material for deforming said layer of material to have a desired shape and for shaping the cavity wall to have a shape corresponding to said desired shape thereby altering the shape of the cavity to facilitate performing endoscopic procedures in the cavity; and joint means within the thickness of said layer of material for allowing passage of an instrument through said layer of material and the cavity wall into the anatomical cavity to facilitate performing endoscopic procedures in the cavity.

12. The apparatus as recited in claim 11 wherein said deforming and shaping means includes protrusions for gripping with a hand to deform said member and shape the cavity wall.

13. The apparatus as recited in claim 12 wherein said layer of material includes a layer of flexible material with a metal material embedded therein.

14. The apparatus as recited in claim 13 wherein said metal material includes bendable metal strips.

15. The apparatus as recited in claim 13 wherein said metal material includes particles of lead.

16. The apparatus as recited in claim 13 wherein said metal material is magnetic.

17. The apparatus as recited in claim 11 wherein said layer of material includes an adhesive coating for attaching said layer to the cavity wall.

18. The apparatus as recited in claim 11 wherein said layer of material is formed of a plurality of connected parts movable relative to each other.

19. Apparatus for stabilizing instruments introduced into an anatomical cavity in the body for performing endoscopic procedures comprising a stabilizer member carrying means for securing the member on an external surface of a wall of the anatomical cavity to allow passage of an instrument through said member and the cavity wall into the anatomical cavity and means for gripping the instrument to stabilize the longitudinal and angular position of the instrument relative to the cavity wall, said stabilizer member being made of a layer of deformable material for changing the shape of the cavity wall in response to deformation of said layer of material, said gripping means including an angularly orienting portion within said layer of material for allowing passage of an instrument through said layer and the cavity wall into the anatomical cavity.

20. The apparatus as recited in claim 19 wherein said angularly orienting portion includes a movable joint for receiving the instrument.

21. Apparatus for stabilizing instruments introduced into an anatomical cavity in the body for performing endoscopic procedures comprising a stabilizer member carrying means for securing the member on an external surface of a wall of the anatomical cavity to allow passage of an instrument through said member and the cavity wall into the anatomical cavity and means for gripping the instrument to stabilize the longitudinal and angular position of the instrument relative to the cavity wall, said stabilizer member being made of deformable material means for changing the shape of the cavity wall in response to deformation of said material means, said gripping means including a movable joint for receiving the instrument, said joint including a rotatable ball member.

22. The apparatus as recited in claim 20 wherein said joint includes a polygonal configured member.

23. The apparatus as recited in claim 20 and further including means for locking said movable joint in position to stabilize the position of the instrument.

24. The apparatus as recited in claim 20 wherein said joint includes a passage for receiving the instrument and an adapter sleeve received in said passage to change the size of said passage.

25. The apparatus as recited in claim 20 wherein said joint includes a passage for receiving the instrument and further including a multiluminal member rotatably mounted in said joint having a plurality of different size lumens therethrough selectively alignable with said passage to receive instruments of different sizes.

26. The apparatus as recited in claim 20 wherein said joint includes a passage through said stabilizer member having cooperating deformable tabs for engaging the instrument.

27. Apparatus for stabilizing instruments introduced into an anatomical cavity in the body for performing endoscopic procedures comprising a stabilizer member carrying means for securing the member on an external surface of a wall of the anatomical cavity to allow passage of an instrument through said member and the cavity wall into the anatomical cavity and means for gripping the instrument to stabilize the longitudinal and angular position of the instrument relative to the cavity wall, said stabilizer member being made of deformable material means for changing the shape of the cavity wall in response to deformation of said material means, said gripping means including a plurality of spaced movable joints for receiving a plurality of instruments.

28. The apparatus as recited in claim 19 and further comprising an adapter block engageable with said stabilizer member at selective locations thereon to allow the instrument to pass through said adapter block and said stabilizer member into the anatomical cavity.

29. The apparatus as recited in claim 28 wherein said adapter block and said stabilizer member carry mating protrusions and recesses for engagement of said adapter block with said stabilizer member.

30. The apparatus as recited in claim 19 wherein said gripping means includes a plurality of nubs protruding from said member.

31. Apparatus for facilitating the performance of endoscopic procedures in an anatomical cavity in the body comprising a deformable, shape-retaining member for attachment to an outer surface of a wall of the cavity, said member being formed of a plurality of portions joined together at frictional joints; and means carried by said member for deforming said member to have a desired shape whereby the cavity wall has a shape corresponding to said desired shape thereby altering the shape of the cavity to facilitate performing endoscopic procedures in the cavity.

* * * * *